US008288504B2

(12) United States Patent
Zawacky et al.

(10) Patent No.: US 8,288,504 B2
(45) Date of Patent: Oct. 16, 2012

(54) METHOD OF MAKING A CYCLIC GUANIDINE FROM DICYANDIAMIDE AND COATING COMPOSITIONS CONTAINING SAME

(75) Inventors: Steven R. Zawacky, Pittsburgh, PA (US); Charles R. Hickenboth, Cranberry Township, PA (US); Richard F. Karabin, Ruffs Dale, PA (US); Gregory J. McCollum, Gibsonia, PA (US); Thomas C. Moriarity, Allison Park, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 99 days.

(21) Appl. No.: 12/720,971

(22) Filed: Mar. 10, 2010

(65) Prior Publication Data

US 2011/0224403 A1    Sep. 15, 2011

(51) Int. Cl.
*C08G 69/00*        (2006.01)

(52) U.S. Cl. .......... 528/327; 528/117; 528/118; 528/62; 528/94; 528/163; 528/216; 528/289; 528/407; 528/423; 528/424

(58) Field of Classification Search .................. 528/327, 528/117, 118, 62, 94, 163, 216, 289, 407, 528/423, 424
See application file for complete search history.

(56) References Cited

U.S. PATENT DOCUMENTS

| 2,473,111 | A | | 6/1949 | Short et al. |
|---|---|---|---|---|
| 3,724,386 | A | * | 4/1973 | Schmidt ..................... 244/159.1 |
| 3,828,122 | A | * | 8/1974 | McPhee et al. .............. 348/170 |
| 3,909,200 | A | | 9/1975 | Redmore |
| 2009/0042060 | A1 | | 2/2009 | Zawacky et al. |
| 2009/0281313 | A1 | | 11/2009 | Minch et al. |
| 2009/0281314 | A1 | | 11/2009 | Boyd et al. |
| 2009/0286978 | A1 | | 11/2009 | Minch et al. |

FOREIGN PATENT DOCUMENTS

WO    2011/079041    6/2011

OTHER PUBLICATIONS

Shestakov et al., "Reaction of Cyanamides with N,N-Binucleophiles", Russian Journal of General Chemistry, 2006, vol. 76, No. 10, pp. 1647-1652.
Dovlatyan et al., "Reactions of Derivatives of Amino- and Mercapto-sym-Triazines with Ethyleneimine and Ethylenediamine", Journal of Heterocyclic Compounds, 1993, vol. 29, pp. 704-707.

* cited by examiner

*Primary Examiner* — Shane Fang
(74) *Attorney, Agent, or Firm* — Alan G Towner; Diane R. Meyers

(57) ABSTRACT

The present invention is directed to a method for preparing a cyclic guanidine comprising reacting (i) a cyanamide, (ii) a polyamine, and (iii) a weak acid. The present invention is also directed to a coating composition comprising the cyclic guanidine.

21 Claims, No Drawings

METHOD OF MAKING A CYCLIC GUANIDINE FROM DICYANDIAMIDE AND COATING COMPOSITIONS CONTAINING SAME

BACKGROUND OF THE INVENTION

1. Field of the Invention

The present invention relates generally to a method for producing a cyclic guanidine and its use in coating compositions.

2. Background Information

Bicyclic guanidines, such as 1,5,7-triazabicyclo[4.40]dec-5-ene (TBD), have chemical activities which make them valuable catalysts for a number of chemical reactions. Published methods for synthesizing bicyclic guanidines, however, are often complicated, involving the use of a multistep synthesis process, and/or require the use of extremely hazardous or prohibitively expensive materials. A method for producing a cyclic guanidine that reduces and/or eliminates hazardous waste streams as well as the need for using hazardous and/or costly raw materials is therefore desired.

SUMMARY OF THE INVENTION

The present invention is directed to a method for preparing a cyclic guanidine comprising reacting (i) cyanamide; (ii) polyamine; and (iii) a weak acid. The present invention is also directed to a coating composition comprising the cyclic guanidine.

The present invention is also directed to a method of making a resin comprising: (a) a cyclic guanidine reaction product of: (i) cyanamide and (ii) a polyamine, and, (iii) a weak acid; (b) an amine; and (c) an epoxy compound.

A method for preparing a cyclic guanidine comprising a six-member ring, the method comprising reacting (i) cyanamide; (ii) a polyamine; and, optionally, (iii) a weak acid. The present invention is also directed to a coating composition comprising the cyclic guanidine.

DETAILED DESCRIPTION OF THE INVENTION

As used herein, unless otherwise expressly specified, all numbers such as those expressing values, ranges, amounts or percentages may be read as if prefaced by the word "about", even if the term does not expressly appear. When referring to any numerical range of values, such ranges are understood to include each and every number and/or fraction between the stated range minimum and maximum. For example, a range of "1 to 10" is intended to include all sub-ranges between (and including) the recited minimum value of 1 and the recited maximum value of 10, that is, having a minimum value equal to or greater than 1 and a maximum value of equal to or less than 10. As employed herein, the term "number" means one or an integer greater than one.

As used herein, plural phrases or terms encompasses their singular counterparts and vice versa, unless specifically stated otherwise. By way of illustration, and not limitation, although reference is made herein to "a" cyanamide, "an" amine, "a" polyamine; "an" epoxy compound; a plurality of these materials may be used in the present invention. As used herein, "plurality" means two or more.

As used herein, "includes" and like terms means "including without limitation."

As used herein, the use of "or" means "and/or" unless specifically stated otherwise, even though "and/or" may be explicitly used in certain instances.

As used herein, "molecular weight" means weight average molecular weight (Mw) as determined by Gel Permeation Chromatography.

As used herein, the term "cure" refers to a process wherein the crosslinkable components of a coating are at least partially crosslinked. In certain embodiments, the crosslink density of the crosslinkable components (i.e., the degree of crosslinking) ranges from 5% to 100%, such as 35% to 85%, or, in some cases, 50% to 85% of complete crosslinking. One skilled in the art will understand that the presence and degree of crosslinking, i.e., the crosslink density, can be determined by a variety of methods, such as dynamic mechanical thermal analysis (DMTA) using a Polymer Laboratories MK III DMTA analyzer conducted under nitrogen.

Reference to any monomer(s) herein refers generally to a monomer that can be polymerized with another polymerizable component such as another monomer or polymer. Unless otherwise indicated, it should be appreciated that once the monomer components react with one another to form a compound, the compound will comprise the residues of such monomer components.

As used herein, "weak acid" means a compound with $5.0 < pKa < 13.5$ as measured in water. For example the pKa of a weak acid can range from $5.5 < pKa < 10.0$.

As used herein, "cyclic guanidine" comprises structures (I) through (V) as well as the salts of such compounds:

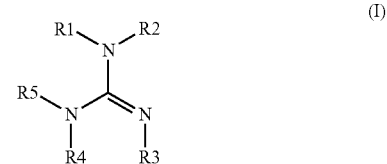

(I)

wherein each of R1, R2, R3, R4, R5 (i.e., substituents of structure (I)) can comprise hydrogen, (cyclo)alkyl, aryl, aromatic, organometallic, a polymeric structure, or together can form a cycloalkyl, aryl, or an aromatic structure, and wherein R1, R2, R3, R4, and R5 can be the same or different. As used herein, "(cyclo)alkyl" refers to both alkyl and cycloalkyl. It will be understood that in the present invention at least two adjacent R groups are connected to form a cyclic moiety, such as the rings in structures (II)-(V) below.

In some embodiments, the double bond between the carbon atom and the nitrogen atom that is depicted in structure (I) may be located between the carbon atom and another nitrogen atom of structure (I). Accordingly, the various substituents of structure (I) may be attached to different nitrogens depending on where the double bond is located within the structure.

In certain embodiments, the cyclic guanidine comprises the guanidine of structure (I) wherein two or more R groups of structure (I) together form one or more rings. In other words, in some embodiments, the cyclic guanidine comprises ≧1 ring. For example, the cyclic guanidine can either be a monocyclic guanidine (1 ring) as depicted in structures (II) and/or (III) below, or the cyclic guanidine can be polycyclic (≧2 rings) as depicted in structures (IV) and (V) below.

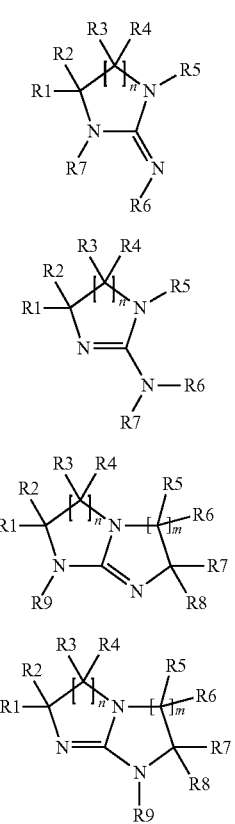

Each substituent of structures (II) and/or (III), R1-R7, can comprise hydrogen, (cyclo)alkyl, aryl, aromatic, organometallic, a polymeric structure, or together can form a cycloalkyl, aryl, or an aromatic structure, and wherein R1-R7 can be the same or different. Similarly, each substituent of structures (IV) and (V), R1-R9, can be hydrogen, alkyl, aryl, aromatic, ogranometallic, a polymeric structure, or together can form a cycloalkyl, aryl, or an aromatic structure, and wherein R1-R9 can be the same or different. Moreover, in some embodiments of structures (II) and/or (III), certain combinations of R1-R7 may be part of the same ring structure. For example, R1 and R7 of structure (II) may form part of a single ring structure. Moreover, in some embodiments, it will be understood that any combination of substituents (R1-R7 of structures (II) and/or (III) as well as R1-R9 of structures (IV) and/or (V)) can be chosen so long as the substituents do not substantially interfere with the catalytic activity of the cyclic guanidine.

In certain embodiments, each ring in the cyclic guanidine is comprised of $\geq 5$-members. For instance, the cyclic guanidine may be a 5-member ring, a 6-member ring, or a 7-member ring. As used herein, the term "member" refers to an atom located in a ring structure. Accordingly, a 5-member ring will have 5 atoms in the ring structure ("n" and/or "m"=1 in structures (II)-(V)), a 6-member ring will have 6 atoms in the ring structure ("n" and/or "m"=2 in structures (II)-(V)), and a 7-member ring will have 7 atoms in the ring structure ("n" and/or "m"=3 in structures (II)-(V)). If the cyclic guanidine is comprised of $\geq 2$ rings (e.g., structures (IV) and (V)), the number of members in each ring of the cyclic guanidine can either be the same or different. For example, one ring may be a five-member ring while the other ring may be a six-member ring. If the cyclic guanidine is comprised of $\geq 3$ rings, then in addition to the combinations cited in the preceding sentence, the number of members in a first ring of the cyclic guanidine can be different from the number of members in any other ring of the cyclic guanidine.

In certain embodiments, the nitrogen atoms of structures (II)-(V) can further have additional atoms attached thereto. Moreover, in some embodiments, the cyclic guanidine can either be substituted or unsubstituted. For example, as used herein in conjunction with the cyclic guanidine, "substituted", in certain embodiments, refers to a cyclic guanidine wherein R5, R6, and/or R7 of structures (II) and/or (III) and/or R9 of structures (IV) and/or (V) is not hydrogen. As used herein in conjunction with the cyclic guanidine, "unsubstituted", in certain embodiments, refers to a cyclic guanidine wherein R1-R7 of structures (II) and/or (III) and/or R1-R9 of structures (IV) and/or (V) is hydrogen. In some embodiments, the substituted cyclic guanidine is 1,5,7-triazabicyclo[4.4.0]dec-5-ene.

Method of Making Cyclic Guanidine

The present invention is directed to a method making a cyclic guanidine. There may be several advantages that may be realized when using the method described herein when compared to other methods known in the art. For example, the method of the present invention could eliminate and/or reduce the amount of waste produced by the disclosed process thereby eliminating and/or reducing the need to manage potential waste streams.

In certain embodiments, the method of the present invention comprises: reacting (i) a cyanamide, (ii) a polyamine, and, (iii) a weak acid. All three of these components are added into a suitable reaction vessel and the reaction is conducted at a temperature ranging from 75° C. to 200° C., such as 100° C. to 120° C., or 120° C. to 140° C., or 140° C. to 160° C., or 150° C. to 180° C., for a time period ranging from 60 to 180 minutes, such as 90 minutes to 150 minutes or 110 minutes to 130 minutes. While ammonia is a typical by-product of the disclosed process, in certain embodiments, the ammonia can be collected and recycled for use in the formation of additional polyamine thereby eliminating a potential waste stream. Alternatively, if the ammonia is not to be recycled, it can be scrubbed and discarded from the process using techniques that are known in the art. Moreover, unlike other processes that may use a carbonate as a reactive ingredient (starting material), the present invention typically does not produce any water, ammonium carbamate, and/or carbonate as by-products. Therefore, the present invention can eliminate and/or reduce the number of waste streams associated with the method disclosed herein.

As used herein, "cyanamide" not only means monomeric cyanamide but it also includes its derivatives as well. An example of a derivative of monomeric cyanamide is dicyandiamide. Accordingly, in some embodiments, the cyanamide used in the various methods disclosed herein is dicyandiamide.

Suitable polyamines that may be used with in the present invention include, without limitation, any polyamine comprising a 1,5,9-triaza nonane moiety. In certain embodiments, the polyamine comprises dipropylene triamine, diethylene triamine, triethylene tetramine, tripropylene tetramine, or combinations thereof.

In some embodiments, the method of the present invention utilizes a weak acid. Suitable weak acids that may be used include, without limitation, phenol, thiol, sulfide, bicarbonate, carbonate, polymerization reaction products of any of the foregoing, or combinations thereof. In certain embodiments, these materials may be polyfunctional. Suitable phenols include, without limitation, bisphenol A, ′butyl phenol, nonylphenol, resorcinol, polymerization reaction products of any of the foregoing, or combinations thereof.

In one embodiment, the reaction process can be depicted in Equation (I) below:

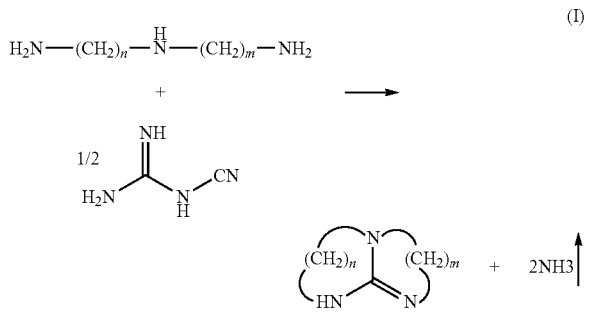

wherein n and m=3.

In another embodiment, the reaction process can be depicted in Equation (II) below:

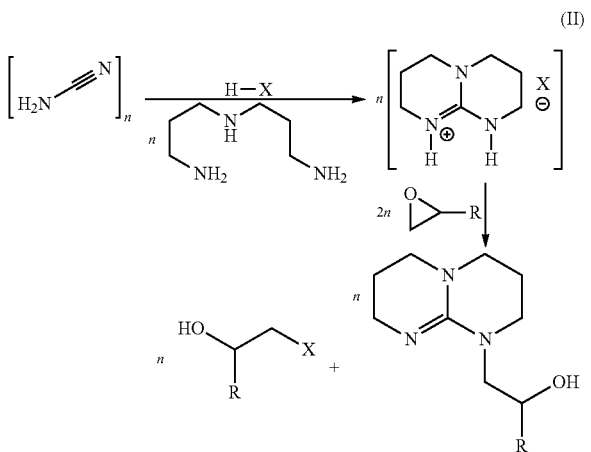

wherein H—X comprises a weak acid; R comprises H or a carbon containing substituent; and wherein n=1 or 2.

In other embodiments, the method for making cyclic guanidine comprises: reacting (i) a cyanamide, (ii) a polyamine, and, optionally, (iii) a weak acid. In these embodiments, the cyclic guanidine that is synthesized will comprise a six-member ring structure. Examples of a cyclic guanidine comprising a six-member ring are depicted in structures (II) to (V) above wherein "n" and/or "m" equal 2.

Method of Making a Polymeric Resin

The present invention is further directed to a method of making a polymeric resin. As will be discussed in greater detail below, the polymeric resin may be used, for example, in an electrodepositable (electrodeposition) coating composition such as those described in U.S. Patent Pub. No. 2009/0042060, which is incorporated herein by reference.

The method of the present invention comprises reacting various ingredients in order to form the polymeric resin. In some embodiments, one of the ingredients used in the method of the present invention is (a) the cyclic guanidine reaction product of (i) a cyanamide, (ii) a polyamine, and (iii) a weak acid. In other embodiments, one of the ingredients used in the method is the 6-member cyclic reaction product of (i) a cyanamide, (ii) a polyamine, and, optionally, (iii) a weak acid, which is described above. Other ingredients that can be reacted with component (a) include, without limitation, (b) an amine and (c) an epoxy compound. After these ingredients are added to a suitable reaction vessel, the reaction is conducted at a temperature ranging from 75° C. to 200° C., such as 100° C. to 120° C., or 120° C. to 140° C., or 140° C. to 160° C., or 150° C. to 180° C., for a time period ranging from 60 to 180 minutes, such as 90 minutes to 150 minutes or 110 minutes to 130 minutes. In certain embodiments, components (a), (b), and (c) are added to a single reaction vessel. Accordingly, in some embodiments, the method disclosed herein can be described as a two-step, single reaction vessel (reaction pot), reaction process. For example, component (c) may be formed by polymerizing various monomers such as bisphenol A diglycidyl ether and bisphenol A. After component (c) is formed, components (a) and (b) are added to the reaction vessel and the reaction is allowed to continue until the desired reaction product is formed. While components (a) and (b) may be added simultaneously, in certain embodiments, these components are added in a sequential order.

The method of making component (a), as well as the various compounds that may be used as components (i), (ii), and (iii), is described in detail in the preceding section entitled "Method of Making Cyclic Guanidine".

Suitable amines that may be used as component (b) not only include the various polyamines described as component (ii) in the preceding paragraphs, but mono-functional amines as well. Suitable mono-functional amines include, without limitation, N-methylethanol amine, diethanol amine, or combinations thereof. Other amines that may be used include, without limitation, 3-dimethylaminopropyl amine, the reaction product of diethylene triamine bis-ketamine and methyl isobutyl ketone, as well as other amines capable of terminating or extending an epoxy resin can be used.

Suitable epoxy compounds that may be used as component (c) include, without limitation, neodecanoic acid glycidyl ester, 2-ethylhexy glycidyl ether, phenyl glycidyl ether, ethylene oxide, propylene oxyide, butylene oxide, epoxidized α-olefins, styrene oxide, and glycidyl ethers of lower monoalcohols such as butyl glycidyl ether and phenyl glycidyl ether. Glycidyl esters of neoacids such as glycidyl neodecanoate or glycidyl pivalate may be used so long as they can be protected from strong acid-forming hydrolysis when added to the cyclic guanidine. In certain embodiments, the epoxy compound is, itself, a polymeric compound. Examples of such a polymeric compound are the epoxy resins that are typically used in cationic electrodepositable coating compositions and which are known in the art.

In some embodiments, a sufficient amount of a polymeric epoxy compound is used so that a majority of the weak acid component (e.g., phenol), the cyclic guanidine, and any additional amines are reacted away. One embodiment of this reaction process is depicted in Equation (III). In this embodiment, the cyclic guanidine is formed via the process described in the section above entitled "Method of Making Cyclic Guanidine".

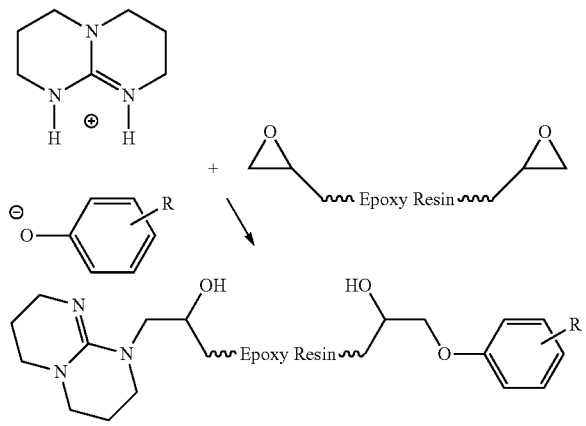

(III)

wherein R comprises H, C, N, chalcogen, halogen, or combinations thereof.

In some embodiments, the method can further comprise reacting components (a), (b), (c), and (d) a polyamine (polyfunctional amine). In certain embodiments, all of these components are added to a single reaction vessel. For example, component (c) may be polymerized from various monomers known in the art such as bisphenol A diglycidyl ether and bisphenol A. After component (c) is formed, components (a), (b), and (d) are added to the reaction vessel and the reaction is allowed to continue until the desired reaction product is formed. While components (a), (b), and (d) may be added simultaneously, in certain embodiments, these components are added in a sequential order. The polyamine used as component (d) can be the same or different from the polyamines described as component (ii) and/or component (b) in the preceding paragraphs. For example, in certain embodiments, a mono-functional amine may be used as component (b) while a polyamine is used as component (d).

In other embodiments, the polymeric resin formed from the method disclosed herein comprises hydroxyl functionality. Therefore, in some embodiments, the polymeric resin may be modified or chain-extended with an isocyanate. Suitable isocyanates that may be used include, without limitation, mono or polyisocyanate compounds that could be used to functionalize or chain extend alcohol functional compounds while maintaining the catalytic activity of the cyclic guanidine. For example, methyl isocyanate, butyl isocyanate, α,α-dimethyl metaisopropenyl benzyl isocyanate (m-TMI), hexamethylene diisocyanate (HDI) isophorone diisocyanate (IPDI), 4,4'-diisocyanatodicyclohexyl methane, toluene diisocyanate (TDI), methylene diphenyl isocyanate (MDI), NCO-functional polymeric versions of any of the foregoing, or combinations thereof, may be used as the isocyanate.

Coating Composition

The present invention is also directed to a coating composition comprising the cyclic guanidine and/or the polymeric resin described in the preceding paragraphs. In some embodiments, the coating composition is an electrodepositable coating composition. The method of the present invention may provide several advantages over conventional methods of making an electrodepositable coating composition. For instance, the present invention allows for the formation of a polymeric resin in a single step as opposed to other methods that require a two step process. This is accomplished due to the fact that unwanted by-products, such as TBD salts of strong acids, are not produced via the method disclosed herein and, therefore, further processing of the reaction product to render the base free is not necessary. In contrast, conventional methods of making the resin disclosed herein require multiple steps, such as isolation and filtering steps, due to the need of having to address the various by-products that arise via those methods, such as metal salts.

In general, an electrodepositable coating composition is made by dispersing a first and second component in an aqueous solution thereby forming the electrodepositable coating composition. A suitable aqueous solution into which the components may be dispersed is water, such as deionized water.

In general, the first component, which can be described as the main vehicle ("clear resin feed"), a film-forming polymer or resin, such as an active hydrogen-containing ionic salt group containing resin and a curing agent (crosslinking agent) that is capable of reacting with the film-forming polymer. The first component may also comprise any additional water-dispersible, non-pigmented components (e.g., catalysts, hindered amine light stabilizers). The film-forming polymer can be the polymeric resin disclosed herein or it can be a combination of the polymeric resin and another film-forming polymer. In addition to the polymeric resin of the present invention, a wide variety of film-forming polymers can be used so long as the polymers are "water dispersible." As used herein, "water dispersible" means that a material is adapted to be solubilized, dispersed, and/or emulsified in water. Examples of film-forming polymers suitable for use in the present invention, without limitation, polymers derived from a polyepoxide, an acrylic, a polyurethane, a polyester, or combinations thereof. In certain embodiments, the film-forming polymer can comprise functional groups. As used herein, "functional groups" or "reactive functional groups" mean hydroxyl, carboxyl, carbamate, epoxy, isocyanate, aceto acetate, amine-salt, mercaptan, or combinations thereof. The film-forming polymers used in the present invention are also ionic in nature. Accordingly, in some embodiments, the film-forming polymer is cationic. In other words, the film-forming polymer comprises cationic salt groups, generally prepared by neutralizing a functional group on the film-forming polymer with an acid, which enables the film-forming polymer to be electrodeposited onto a cathode. For example, in some embodiments, a film-forming cationic polymer can be derived by reacting a polyepoxide containing polymer with a cationic salt group former. As used herein, "cationic salt group former" means a material that is reactive with epoxy groups and which can be acidified before, during, or after reaction with the epoxy groups to form cationic salt groups. Suitable materials that can be used as the cationic salt group former include, without limitation, amines such as primary or secondary amines, which can be acidified after reaction with the epoxy groups to form amine salt groups, or tertiary amines, which can be acidified prior to reaction with the epoxy groups and which after reaction with the epoxy groups, form quaternary ammonium salt groups. Examples of other cationic salt group formers are TBD and sulfides (e.g., thioethers) which can be mixed with acid prior to reaction with the epoxy groups and form ternary sulfonium salt groups upon subsequent reaction with the epoxy groups.

As stated above, the first component also comprises a curing agent that is reactive towards that film-forming resin described in the preceding paragraph. For example, the film-forming agent may comprise moieties that are reactive with the functional groups of the film-forming polymer. Suitable crosslinking agents that may be used include, without limitation, aminoplasts, polyisocyanates (including blocked isocyanates), polyepoxides, beta-hydroxyalkylamides, polyacids, anhydrides, organometallic acid-functional materials, polyamines, polyamides, cyclic carbonates, siloxanes, or combinations thereof. In some embodiments, the curing agent can comprise from 30 weight % to 40 weight % based on the total resin solids of the electrodepositable coating composition.

The first component may further comprise a curing catalyst that may be used to catalyze the reaction between the crosslinking agent and the film-forming polymer. In certain embodiments, the cyclic guanidine disclosed herein may act as a curing catalyst. Accordingly, in some embodiments, the polymeric resin, which contains the cyclic guanidine, can be self-catalyzing by maintaining the catalytic activity of the cyclic guanidine moiety. One advantage that might be derived from using the polymeric resin in a coating composition, such as an electrodepositable coating composition, is that additional curing catalysts may not be needed in order to catalyze the curing reaction since the polymeric resin itself can catalyze the reaction. Alternatively, if other curing catalysts are used in combination with the polymeric resin, it might be possible to reduce the amount of these other catalysts in the composition since the polymeric resin already comprises a catalytic moiety.

Examples of the other curing catalysts that may be used in the present invention include, without limitation, organotin compounds (e.g., dibutyltin oxide, dioctyltin oxide) and salts thereof (e.g., dibutyltin diacetate); other metal oxides (e.g., oxides of cerium, zirconium and/or bismuth) and salts thereof (e.g., bismuth sulfamate and/or bismuth lactate), or combinations thereof.

In general, the second component, which can be described as the grind vehicle ("pigment paste"), comprises a pigment (e.g., titanium dioxide, carbon black), a water-dispersible grind resin that comprises a polymer, which can be the same or different from the film-forming polymer described above, and, optionally, additives such as catalysts (e.g., the other catalysts described in the preceding paragraph), antioxidants, biocides, defoamers, surfactants, wetting agents, dispersing aids, clays, hindered amine light stabilizers, UV light absorbers and stabilizers, a stabilizing agent, or combinations thereof. All of these materials are known to those skilled in the art.

While the preceding paragraphs described the cyclic guanidine disclosed herein as being in the first component, the cyclic guanidine can also be incorporated into the second component and/or post added to the electrodepositable coating composition after it has been made. Accordingly, depending on the user's preference, the cyclic guanidine can be incorporated into any of the components used to make the electrodepositable coating composition.

Coating System

The coating composition comprising the cyclic guanidine and/or polymeric resin of the present invention may be applied alone or as part of a coating system that can be deposited onto a number of different substrates. The coating system typically comprises a number of coating layers. A coating layer is typically formed when a coating composition that is deposited onto the substrate is substantially cured by methods known in the art (e.g., by thermal heating).

Suitable substrates that can be coated with the electrodepositable coating composition of the present invention include, without limitation, metal substrates, metal alloy substrates, and/or substrates that have been metallized, such as nickel plated plastic. In some embodiments, the metal or metal alloy can be aluminum and/or steel. For example, the steel substrate could be cold rolled steel, electrogalvanized steel, and hot dipped galvanized steel. Moreover, in some embodiments, the substrate may comprise a portion of a vehicle such as a vehicular body (e.g., without limitation, door, body panel, trunk deck lid, roof panel, hood, and/or roof) and/or a vehicular frame. As used herein, "vehicle" or variations thereof includes, but is not limited to, civilian, commercial, and military land vehicles such as cars, motorcycles, and trucks. It will also be understood that, in some embodiments, the substrate may be pretreated with a pretreatment solution, such as a zinc phosphate solution as described in U.S. Pat. Nos. 4,793,867 and 5,588,989. Alternatively, in other embodiments, the substrate is not pretreated with a pretreatment solution prior to coating the substrate with the coating composition described herein.

In certain embodiments, the coating composition is an electrodepositable coating composition comprising the cyclic guanidine and/or polymeric resin described above. The electrodepositable coating composition may be applied over a bare (i.e., non-pretreated) substrate or it can be applied to a substrate that has been pretreated. After the electrodepositable coating composition is cured, a primer-surfacer coating composition is applied onto at least a portion of the electrodepositable coating composition. The primer-surfacer coating composition is typically applied to the electrodepositable coating layer and cured prior to a subsequent coating composition being applied over the primer-surfacer coating composition.

The primer-surfacer layer that results from the primer-surfacer coating composition serves to enhance chip resistance of the coating system as well as aid in the appearance of subsequently applied layers (e.g., color imparting coating composition and/or substantially clear coating composition). As used herein, "primer-surfacer" refers to a primer composition for use under a subsequently applied coating composition, and includes such materials as thermoplastic and/or crosslinking (e.g., thermosetting) film-forming resins generally known in the art of organic coating compositions. Suitable primers and primer-surfacer coating compositions include spray applied primers, as are known to those skilled in the art. Examples of suitable primers include several available from PPG Industries, Inc., Pittsburgh, Pa., as DPX-1791, DPX-1804, DSPX-1537, GPXH-5379, OPP-2645, PCV-70118, and 1177-225A. Another suitable primer-surfacer coating composition that can be utilized in the present invention is the primer-surfacer described in U.S. patent application Ser. No. 11/773,482, which is incorporated in its entirety herein by reference.

It should be noted that in some embodiments, the primer-surfacer coating composition is not used in the coating system. Therefore, a color-imparting basecoat coating composition can be applied directly onto the cured electrodepositable coating composition.

In some embodiments, a color-imparting coating composition (hereinafter, "basecoat") is deposited onto at least a portion of the primer surfacer coating layer, if present. Any basecoat coating composition known in the art may be used in the present invention. It should be noted that these basecoat coating compositions typically comprise a colorant.

In certain embodiments, a substantially clear coating composition (hereinafter, "clearcoat") is deposited onto at least a portion of the basecoat coating layer. As used herein, a "substantially clear" coating layer is substantially transparent and not opaque. In certain embodiments, the substantially clear coating composition can comprise a colorant but not in an amount such as to render the clear coating composition opaque (not substantially transparent) after it has been cured. Any clearcoat coating composition known in the art may be used in the present invention. For example, the clearcoat coating composition that is described in U.S. Pat. Nos. 5,989,642, 6,245,855, 6,387,519, and 7,005,472, which are incorporated in their entirety herein by reference, can be used in the coating system. In certain embodiments, the substantially clear coating composition can also comprise a particle, such as a silica particle, that is dispersed in the clearcoat coating composition (such as at the surface of the clearcoat coating composition after curing).

One or more of the coating compositions described herein can comprise colorants and/or other optional materials, which are known in the art of formulated surface coatings. As used herein, the term "colorant" means any substance that imparts color and/or other opacity and/or other visual effect to the composition. The colorant can be added to the coating in any suitable form, such as discrete particles, dispersions, solutions and/or flakes (e.g., aluminum flakes). A single colorant or a mixture of two or more colorants can be used in the coating composition described herein.

Example colorants include pigments, dyes and tints, such as those used in the paint industry and/or listed in the Dry Color Manufacturers Association (DCMA), as well as special effect compositions. A colorant may include, for example, a finely divided solid powder that is insoluble but wettable under the conditions of use. A colorant can be organic or inorganic and can be agglomerated or non-agglomerated. Colorants can be incorporated into the coatings by use of a grind vehicle, such as an acrylic grind vehicle, the use of which will be familiar to one skilled in the art.

Example pigments and/or pigment compositions include, but are not limited to, carbazole dioxazine crude pigment, azo, monoazo, disazo, naphthol AS, salt type (lakes), benzimidazolone, condensation, metal complex, isoindolinone, isoindoline and polycyclic phthalocyanine, quinacridone, perylene, perinone, diketopyrrolo pyrrole, thioindigo, anthraquinone, indanthrone, anthrapyrimidine, flavanthrone, pyranthrone, anthanthrone, dioxazine, triarylcarbonium, quinophthalone pigments, diketo pyrrolo pyrrole red ("DPPBO red"), titanium dioxide, carbon black and mixtures thereof. The terms "pigment" and "colored filler" can be used interchangeably.

Example dyes include, but are not limited to, those that are solvent and/or aqueous based such as phthalo green or blue, iron oxide, bismuth vanadate, anthraquinone, perylene, aluminum and quinacridone.

Example tints include, but are not limited to, pigments dispersed in water-based or water miscible carriers such as AQUA-CHEM 896 commercially available from Degussa, Inc., CHARISMA COLORANTS and MAXITONER INDUSTRIAL COLORANTS commercially available from Accurate Dispersions division of Eastman Chemical, Inc.

As noted above, the colorant can be in the form of a dispersion including, but not limited to, a nanoparticle dispersion. Nanoparticle dispersions can include one or more highly dispersed nanoparticle colorants and/or colorant particles that produce a desired visible color and/or opacity and/or visual effect. Nanoparticle dispersions can include colorants such as pigments or dyes having a particle size of less than 150 nm, such as less than 70 nm, or less than 30 nm. Nanoparticles can be produced by milling stock organic or inorganic pigments with grinding media having a particle size of less than 0.5 mm. Example nanoparticle dispersions and methods for making them are identified in U.S. Pat. No. 6,875,800, which is incorporated herein by reference. Nanoparticle dispersions can also be produced by crystallization, precipitation, gas phase condensation, and chemical attrition (i.e., partial dissolution). In order to minimize re-agglomeration of nanoparticles within the coating, a dispersion of resin-coated nanoparticles can be used. As used herein, a "dispersion of resin-coated nanoparticles" refers to a continuous phase in which discreet "composite microparticles", which comprise a nanoparticle and a resin coating on the nanoparticle, is dispersed. Example dispersions of resin-coated nanoparticles and methods for making them are identified in U.S. Patent Application Publication 2005-0287348, filed Jun. 24, 2004, U.S. Provisional Application No. 60/482,167 filed Jun. 24, 2003, and U.S. patent application Ser. No. 11/337,062, filed Jan. 20, 2006, which is also incorporated herein by reference.

Example special effect compositions that may be used include pigments and/or compositions that produce one or more appearance effects such as reflectance, pearlescence, metallic sheen, phosphorescence, fluorescence, photochromism, photosensitivity, thermochromism, goniochromism and/or color-change. Additional special effect compositions can provide other perceptible properties, such as opacity or texture. In a non-limiting embodiment, special effect compositions can produce a color shift, such that the color of the coating changes when the coating is viewed at different angles. Example color effect compositions are identified in U.S. Pat. No. 6,894,086, incorporated herein by reference. Additional color effect compositions can include transparent coated mica and/or synthetic mica, coated silica, coated alumina, a transparent liquid crystal pigment, a liquid crystal coating, and/or any composition wherein interference results from a refractive index differential within the material and not because of the refractive index differential between the surface of the material and the air.

In certain non-limiting embodiments, a photosensitive composition and/or photochromic composition, which reversibly alters its color when exposed to one or more light sources, can be used in the coating composition described herein. Photochromic and/or photosensitive compositions can be activated by exposure to radiation of a specified wavelength. When the composition becomes excited, the molecular structure is changed and the altered structure exhibits a new color that is different from the original color of the composition. When the exposure to radiation is removed, the photochromic and/or photosensitive composition can return to a state of rest, in which the original color of the composition returns. In one non-limiting embodiment, the photochromic and/or photosensitive composition can be colorless in a non-excited state and exhibit a color in an excited state. Full color-change can appear within milliseconds to several minutes, such as from 20 seconds to 60 seconds. Example photochromic and/or photosensitive compositions include photochromic dyes.

In a non-limiting embodiment, the photosensitive composition and/or photochromic composition can be associated with and/or at least partially bound to, such as by covalent bonding, a polymer and/or polymeric materials of a polymerizable component. In contrast to some coatings in which the photosensitive composition may migrate out of the coating and crystallize into the substrate, the photosensitive composition and/or photochromic composition associated with and/or at least partially bound to a polymer and/or polymerizable component in accordance with a non-limiting embodiment of the present invention, have minimal migration out of the coating. Example photosensitive compositions and/or photochromic compositions and methods for making them are identified in U.S. application Ser. No. 10/892,919, filed Jul. 16, 2004.

In general, the colorant can be present in any amount sufficient to impart the desired visual and/or color effect. The colorant may comprise from 1 to 65 weight percent of the present compositions, such as from 3 to 40 weight percent or 5 to 35 weight percent, with weight percent based on the total weight of the compositions.

One or more of the coating compositions described herein can comprise other optional materials well known in the art of formulated surface coatings, such as plasticizers, anti-oxidants, hindered amine light stabilizers, UV light absorbers and stabilizers, surfactants, flow control agents, thixotropic agents such as bentonite clay, pigments, fillers, organic cosolvents, catalysts, including phosphonic acids and other customary auxiliaries.

In addition to the materials described above, one or more of the coating compositions described above can also comprise an organic solvent. Suitable organic solvents that can be used in the coating composition include any of those listed in the preceding paragraphs as well as butyl acetate, xylene, methyl ethyl ketone, or combinations thereof.

It will be further appreciated that one or more of the coating compositions that form the various coating layers described herein can be either "one component" ("1K"), "two component" ("2K"), or even multi-component compositions. A 1K composition will be understood as referring to a composition wherein all of the coating components are maintained in the same container after manufacture, during storage, etc. A 2K composition or multi-component composition will be understood as referring to a composition wherein various components are maintained separately until just prior to application. A 1K or 2K coating composition can be applied to a substrate and cured by any conventional means, such as by heating, forced air, and the like.

The coating compositions that form the various coating layers described herein can be deposited or applied onto the substrate using any technique that is known in the art. For example, the coating compositions can be applied to the substrate by any of a variety of methods including, without limitation, spraying, brushing, dipping, and/or roll coating, among other methods. When a plurality of coating compositions are applied onto a substrate, it should be noted that one coating composition may be applied onto at least a portion of an underlying coating composition either after the underlying coating composition has been cured or prior to the underlying coating composition being cured. If the coating composition is applied onto an underlying coating composition that has not been cured, both coating compositions may be cured simultaneously.

The coating compositions may be cured using any technique known in the art such as, without limitation, thermal energy, infrared, ionizing or actinic radiation, or by any combination thereof. In certain embodiments, the curing operation can be carried out at temperatures $\geq 10°$ C. In other embodiments, the curing operation can be carried out at temperature $\leq 246°$ C. In certain embodiments, the curing operation can carried out at temperatures ranging between any combination of values, which were recited in the preceding sentences, inclusive of the recited values. For example, the curing operation can be carried out at temperatures ranging from 120° C.-150° C. It should be noted, however, that lower or higher temperatures may be used as necessary to activate the curing mechanisms.

In certain embodiments, one or more of the coating compositions described herein is a low temperature, moisture curable coating compositions. As used herein, the term "low temperature, moisture curable" refers to coating compositions that, following application to a substrate, are capable of curing in the presence of ambient air, the air having a relative humidity of 10% to 100%, such as 25% to 80%, and a temperature in the range of $-10°$ C. to 120° C., such as 5° C. to 80° C., in some cases 10° C. to 60° C. and, in yet other cases, 15° C. to 40° C.

The dry film thickness of the coating layers described herein can range from 0.1 micron to 500 microns. In other embodiments, the dry film thickness can be $\leq 125$ microns, such as 80 microns. For example, the dry film thickness can range from 15 microns to 60 microns.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

EXAMPLES

Example 1

Preparation of Cyclic Guanidine, No Weak Acid

| # | Material | Parts by Weight (g) |
|---|----------|---------------------|
| 1 | dicyandiamide | 42.0 |
| 2 | Butyl cellosolve | 125.4 |
| 3 | Dipropylene triamine | 131.2 |

Materials 1 and 2 were added to a round bottom flask equipped with a mechanical stirrer, reflux condenser, temperature probe and inert gas inlet. The mixture was then warmed to 60° C., at which time material 3 was added and the mixture held at 60° C. for 1 hour (h). The mixture was then warmed to 170° C. and sampled hourly. After one hour at temperature all the dicyandiamide had been consumed. A $^{13}$C NMR analysis of the cooled product indicates that the dicyandiamide had been converted in 34% yield to 1,5,7-triazabicyclo[4.4.0]dec-5-ene and 47% yield 2,4,6-triamino-s-triazine or melamine as a side product.

Example 2

Preparation of Cyclic Guanidine Under CO2

| # | Material | Parts by Weight (g) |
|---|----------|---------------------|
| 1 | dicyandiamide | 42.0 |
| 2 | Butyl cellosolve | 125.4 |
| 3 | Dipropylene triamine | 131.2 |

Materials 1 and 2 were added to a round bottom flask equipped with a mechanical stirrer, reflux condenser, temperature probe and a gas inlet. The mixture was placed under an atmosphere of carbon dioxide and then warmed to 60° C., at which time material 3 was added dropwise over 60 minutes. The mixture was then warmed to 130° C., held there and sampled hourly. After 5 hours essentially all the dicyandiamide had been consumed. A $^{13}$C NMR analysis of the cooled product indicated that the dicyandiamide had been converted in 57% yield to 1,5,7-triazabicyclo[4.4.0]dec-5-ene. No 2,4,6-triamino-s-triazine or melamine side product was observed.

Example 3

Cyclic Guanidine-BPA Salt

| # | Material | Parts by Weight (g) |
|---|----------|---------------------|
| 1 | dicyandiamide | 100.9 |
| 2 | Butyl cellosolve | 470.0 |
| 3 | Bisphenol A | 456.6 |
| 4 | Dipropylene triamine | 262.4 |

Materials 1 and 2 were added to a round bottom flask equipped with a mechanical stirrer, reflux condenser, temperature probe and inert gas inlet. The mixture was then warmed to 60° C. , at which time material 3 was added. Material 4 was then added over 30 min, and a mild exotherm of less than 5° C. was observed. The mixture was then warmed to 171° C., and ammonia evolution was monitored using pre-moistened pH paper. After ammonia evolution slowed (approximately 1.5 h at 171° C.), the reaction was cooled. $^{13}C$ NMR analysis of the cooled product indicates that the reaction mixture consists of 17.6 wt % 1,5,7-triazabicyclo[4.4.0]dec-5-ene, 38 wt % bisphenol A, 3.1 wt % dipropylene triamine, 40.3 wt % butyl cellosolve, and 1.1wt % melamine. HPLC analysis under acidic aqueous conditions indicated that the final reaction mixture contained 18.4 wt % TBD. The overall yield of TBD was estimated at 76%.

Example 4

Polyurethane Crosslinker

| | | parts by weight |
|---|---|---|
| 1 | LUPRANATE M20[1] | 1340.00 |
| 2 | dibutyltin dilaurate | 1.00 |
| 3 | methylisobutyl ketone | 306.04 |
| 4 | butyl Cellosolve | 236.00 |
| 5 | MACOL 98B[2] | 246.50 |
| 6 | methanol | 225.60 |
| | TOTAL | 2355.14 |

[1]Isocyanate available from BASF Corp.
[2]Bisphenol A ethoxylate of hydroxyl equivalent weight approximately 245 available from BASF Corp.

1, 2, and 3 were charged into a reaction vessel under a nitrogen atmosphere. Charge 4 was added over about 1 hour allowing the temperature to increase to 50° C. Charge 5 was then added slowly allowing the reaction mixture to exotherm to 65° C. The mixture was then held until the isocyanate equivalent weight was 304±10. The nitrogen flow was then stopped and charge 6 was added at a controlled rate allowing the reaction mixture to exotherm to a maximum of 100° C. The mixture was then held at 100° C. until the infrared spectrum indicated no residual isocyanate. The mixture had a measured solids content of 87%.

Example 5

Cationic Resin Made with TBD from Example 3

| # | Material | parts |
|---|----------|-------|
| 1 | EPON 828[1] | 614.68 |
| 2 | Bisphenol A | 135.75 |
| 3 | MACOL 98 A MOD 1[2] | 204.16 |
| 4 | Methylisobutyl ketone (mibk) | 29.52 |
| 5 | Ethyltriphenyl phosphonium iodide | 0.60 |
| 6 | MACOL 98 A MOD 1[2] | 86.84 |
| 7 | Methylisobutyl ketone (mibk) | 62.52 |
| 8 | Ketimine[3] | 20 |
| 9 | N-methyl ethanolamine | 18.03 |
| 10 | TBD solution from example 3 | 341.06 |
| 11 | Glacial acetic acid | 16.59 |
| 12 | Polyurethane from example 4 | 1081.88 |
| 13 | 90% formic acid | 22.97 |
| 14 | $H_2O$ | 1485.84 |
| 15 | $H_2O$ | 1414.34 |
| 16 | $H_2O$ | 1040.0 |

[1]Epoxy resin available from Hexion Specialty Chemicals.
[2]Bisphenol ethylene oxide adduct available from BASF Corporation.
[3]MIBK diketimine of diethylene triamine at 72.7% in MIBK.
[4]30% by weight solution of gum rosin in diethylene glycol mono butyl ether formal.

Materials 1, 2, 3, 4 and 5 were charged to a 4 neck round bottom flask, fit with a stirrer, temperature measuring probe, $N_2$ blanket and heated to 130° C. The mixture exothermed to about 150° C. The temperature was allowed to drop to 145° C. and held at this temperature for 2 hours. Charges 6 and 7 were then added. Charges 8, 9 and 10 were added and the mixture was held at 122° C. for 1 h. Material 11 was then added slowly, followed by 10 min of mixing and then material 12 was added. After a 10 minutes of mixing, 2330.11 parts of the reaction mixture was poured into a solution of materials 13 and 14 with stirring. Charge 15 was then added and the resulting dispersion is mixed for thirty minutes and then charge 15 is added with stirring over about 30 minutes and mixed well. Charge 16 is added and mixed well. About 1040 parts of water and solvent were distilled off under vacuum at 60-65° C. The resulting aqueous dispersion had a solids content of 41.8%.

Example 6

| Material # | Material | Parts by weight |
|---|----------|-----------------|
| 1 | DER-732[1] | 711 |
| 2 | Bisphenol A | 172 |
| 3 | Benzyldimethyl amine | 1.65 |
| 4 | Butoxyethanol | 58.8 |
| 5 | JEFFAMINE D400[2] | 184.7 |
| 6 | EPON 828[3] | 19.1 |
| 7 | Butoxyethanol | 3.4 |
| 8 | Deionized water | 1047 |
| 9 | Acetic Acid | 19 |
| 10 | Deionized water | 1030 |

[1]Aliphatic epoxy resin available from Dow Chemical Co.
[2]Polyoxypropylene diamine available from Huntsman Corp.
[3]A difunctional bisphenol A/epichlorohydrin derived liquid epoxy resin available from Hexion Specialty Chemical Material 1 and 2 were charged to a suitably equipped 3-liter round-bottomed flask. The mixture was heated to 130° C. and material 3 was added. The reaction mixture was held at 135° C. until the epoxide equivalent weight of the mixture was 1232. Material 4 was added and then the mixture was cooled to 95° C. Material 5 was added and the reaction held at 95° C. until the Gardner-Holdt viscosity of a sample of the resin diluted 50% solids in methoxy propanol was "H-J". A mixture of material 6 and 7 was added and the mixture held until the Gardner-Holdt viscosity of a sample of the resin diluted to 50% solids in methoxy propanol is "Q-". 989 g of this resin was poured into a mixture of material 8 and 9 and mixed for 30 minutes. 1030 g deionized water (material 10) was then added and mixed well. The final aqueous dispersion had a measured solids content of 30%.

Example 7

| Material # | Material | Parts by weight |
|---|---|---|
| 1 | EPON 828[1] | 1023 |
| 2 | MACOL 98B[2] | 365 |
| 3 | Bisphenol A | 297 |
| 4 | 2-Butoxyethanol | 187.2 |
| 5 | Benzyldimethylamine | 1.4 |
| 6 | Benzyldimethylamine | 3.0 |
| 7 | Diketimine[3] | 182.3 |
| 8 | N-methylethanolamine | 85.2 |
| 9 | Acetic Acid | 105.9 |
| 10 | Deionized water | 1065.9 |
| 11 | Deionized water | 735.9 |
| 12 | Deionized water | 1156.4 |
| 13 | Deionized water | 867.3 |

[1]A difunctional bisphenol A/epichlorohydrin derived liquid epoxy resin available from Hexion Specialty Chemical
[2]Bisphenol A ethoxylate of hydroxyl equivalent weight approximately 245 available from BASF Corp.
[3]MIBK diketimine of diethylene triamine at 72.7% in MIBK.

EPON 828, bisphenol A-ethylene oxide adduct, bisphenol A and 2-butoxyethanol were charged into a reaction vessel and heated under a nitrogen atmosphere to 125° C. The first portion of the benzyldimethylamine was added and the reaction allowed to exotherm to around 180° C. During the exotherm when the reaction reached 160° C., a one hour hold was started. After the peak exotherm, the resin was allowed to cool back to 160° C., continuing the hold. After the hold, the reaction was then cooled to 130° C. At 130° C. the second portion of benzyldimethylamine was added. The reaction was held at 130° C. until an extrapolated epoxy equivalent weight of 1070. At the expected epoxy equivalent weight, diketimine and N-methylethanolamine were added in succession and the mixture allowed to exotherm to around 150° C. At the peak exotherm a one hour hold was started while allowing the reaction to cool to 125° C. After the one hour hold the resin was dispersed in an aqueous medium containing acetic acid and the first portion of deionized water. The dispersion was later reduced with the second, third, and fourth portions of deionized water. The resulting cationic soap was vacuum striped until the methyl isobutyl ketone liberated by the hydrolysis of the diketime was less than 0.05%. The solids f the aqueous solution was adjusted to 26%.

443 g of deionized water was then added to 2517 g of the above aqueous polymer solution. The mixture was heated to 70° C. under a nitrogen blanket. 44.8 g of an 85% solution of Epon 828 in mibk was then added over 15 minutes with agitation. 4.05 g of mibk was added as a rinse for the Epon 828 solution and the mixture held at 70° C. for 45 minutes. The mixture was heated to 90° C. over 70 minutes and held at this temperature for 3 hours with mixing. 337 g of deionized water was then added and the dispersion cooled to less than 35° C. and poured out. The measured solids content was 18.89%

Example 8

| # | Material | Parts by weight |
|---|---|---|
| 1 | EPON 828[1] | 533.2 |
| 2 | nonyl phenol | 19.1 |
| 3 | bisphenol A | 198.3 |
| 4 | ethyltriphenyl phosphonium iodide | 0.7 |
| 5 | butoxy propanol | 99.3 |
| 6 | butoxy propanol | 93.9 |
| 7 | methoxy propanol | 50.3 |
| 8 | thiodiethanol | 121.3 |
| 9 | butoxy propanol | 6.9 |
| 10 | deionized water | 32.1 |
| 11 | dimethylol propionic acid | 133.1 |
| 12 | Deionized water | 1100 |
| 13 | Deionized water | 790 |

[1]Diglycidyl ether of Bisphenol A commercially available from Resolution Chemical Co as Epon 828.

Materials 1 through 5 were charged to a suitably equipped flask and heat to 125° C. The mixture was allowed to exotherm to 175° C. and then held at 160-165° C. for 1 hr. After the 1 hr hold, materials 6-7 were added. The mixture was then cooled to 80° C., then materials 8-11 were added. The mixture was then held at 78° C. until the measured acid value is less than 2. When the acid value is less than 2, 1288.2 g of the resin was poured into 1100 g of deionized water (material 12) with stirring. Mix for 30 minutes then add material 13 and mix well.

Example 9

| Material | Description | Parts by weight |
|---|---|---|
| 1 | Cationic resin[1] | 25.85 |
| 2 | Cationic resin from Example 8 | 30.6 |
| 3 | Deionized water | 32.55 |
| 4 | Silica[2] | 11 |

[1]Cationic resin from Example II of U.S. Pat. No. 4,007,154.
[2]Available from Evonik pigments as OK-607

Materials 1 through 3 were blended in an appropriate container for cowels dispersion. Material 4 was then added under high speed cowels dispersion. The pigment was dispersed then ground until a particle size, as measured by a Hegman gauge, of 12-14 microns was observed.

Example 10

Pigment Paste

| Material | Description | Parts by Weight |
|---|---|---|
| 1 | Cationic resin from Example 8 | 12.8 |
| 2 | Cationic resin[1] | 2.8 |
| 3 | Deionized water | 2.74 |
| 4 | Ethylene glycol monobutyl ether | 0.8 |
| 5 | Titanium Dioxide[2] | 21.1 |
| 6 | Carbon Black | 0.09 |
| 7 | Tin Dioxide powder | 0.20 |

-continued

| Material | Description | Parts by Weight |
|---|---|---|
| 8 | Pigment paste from Example 9 | 55 |
| 9 | Deionized Water | 4.47 |

[1]Cationic resin from Example II of U.S. Pat. No. 4,007,154.

[2]Available from KRONOS as 2305 or DUPONT as R900

[3]Printex 200 available from Evonik Pigments

Materials 1 through 4 were blended in a container appropriate for a cowels dispersion. Materials 5, 6, and 7 were then added under high speed cowels dispersion and the resulting pigment dispersion was held under high speed cowels dispersion for 20 minutes. The dispersion was then transferred to a Vertical mill equipped with 1-1.6 mm zircoa beads and milled until a particle size of 8-10 microns was observed using a Hegman gauge. The mill time was approximately 30 minutes. Material 8 was then blended into the resulting pigment dispersion under low shear and material 9 was added to bring the resulting pigment dispersion to a total solids of 45.31%.

Example 11

| Material # | Material | Parts by Weight |
|---|---|---|
| 1 | EPON 828 | 553.2 |
| 2 | Bisphenol A | 238.9 |
| 3 | MACOL 98B[1] | 112.5 |
| 4 | Methyl Isobutyl Ketone | 18.5 |
| 5 | Ethyl triphenyl phosphonium iodide | 0.5 |
| 6 | MACOL 98B[1] | 36.9 |
| 7 | Methyl Isobutyl Ketone | 21.1 |
| 8 | Crosslinker (Example 4) | 1079.2 |
| 9 | Diketimine[2] | 51.3 |
| 10 | Diethanol Amine | 61.2 |
| 11 | Formic Acid | 28 |
| 12 | Deionized Water | 1355.1 |
| 13 | Deionized Water | 1049 |
| 14 | Deionized Water | 1200 |

[1]Bisphenol A ethoxylate of hydroxyl equivalent weight approximately 245 available from BASF Corp.
[2]MIBK diketimine of diethylene triamine at 72.7% in MIBK.

Materials 1 through 5 were charged sequentially into a 3 neck flask equipped with a mechanical stirrer, condenser nitrogen purge, temperature controller and a heating mantel. The reaction was allowed to exotherm, and is then held at 145 C for 2 hrs. Material 6 was then added and stirred for 15 minutes. Material 7 and 8 were added sequentially and allowed to stir for 15 minutes. Materials 9 and 10 were then added and the reaction was allowed to exotherm, and then it was held at 125 C for 1 hr. The resulting cationic resin was then dispersed by adding the resin to a solution of materials 11 and 12 under agitation. The dispersion was allowed to stir for 30 minutes, then material 13 was added slowly and the dispersion is stirred for an additional 30 minutes. Material 14 was then added to reduce the resin to final solids. MIBK was then removed by heating to a temperature of 60-65° C. and vacuum distilling off 1200 grams of water/MIBK.

Example 12

Surfactant Blend

| Material # | Description | Parts by Weight |
|---|---|---|
| 1 | 2-butoxyethanol | 31.26 |
| 2 | SURFYNOL 104 | 31.26 |
| 3 | Amine C[1] | 32.46 |
| 4 | 75% Acetic acid in Water | 5.01 |

[1]4,5-Dihydro - 1H-Imidazole-1-ethanol available from Ciba Geigy

Materials 1 through 4 were blended sequentially.

Example 13

| Material # | Description | Parts by Weight |
|---|---|---|
| 1 | MAZEEN 355 70[1] | 1423.49 |
| 2 | acetic acid | 15.12 |
| 3 | Dibutyltindilaurate | 1.52 |
| 4 | Toluene diisocyanate 80/20 | 200.50 |
| 5 | acetic acid | 49.32 |
| 6 | Deionized water | 1623.68 |
| 7 | Deionized water | 766.89 |

[1]Amine functional diol of amine equivalent weight 1131 available from BASF Corporation Materials 1 and 2 were charged to a 4 neck round bottom flask, fit with a stirrer, temperature measuring probe and $N_2$ blanket and mixed for 10 minutes. Material 3 was added and then material 4 was charged over about 1 hour allowing the reaction mixture to exotherm to a maximum temperature of 100° C. The mixture was then held at 100° C. until the infrared spectrum indicates the absence of isocyanate (approximately 1 hour). 1395 g of the reaction mixture was then poured into a mixture of materials 5 and 6 and mixed for 1 hour. Material 7 was then added over about 1 hour and mixed for about 1 hour. The resulting aqueous solution had a solids content of about 36%.

Example 14

| | | Parts by Weight | |
|---|---|---|---|
| Material # | Description | Paint A | Paint B |
| 1 | Cationic resin from Example 6 | 159.14 | 58.63 |
| 2 | Resin from example 11 | 65.4 | 0 |
| 3 | Cationic resin from Example 7 | 116.04 | 48.86 |
| 4 | Propylene glycol Phenyl ether | 11.94 | 8.79 |
| 5 | Ethylene glycol hexyl ether | 0 | 17.59 |
| 6 | MAZON 1651[1] | 0 | 15.39 |
| 7 | NORAMOX C5[2] | 0 | 2.26 |
| 8 | Surfactant Blend from example 12 | 4.66 | 3.54 |
| 9 | Cationic resin from Example 11 | 0 | 904.03 |
| 10 | Cyclic guanidine-containing catalyst resin from Example 5 | 1170.7 | 0 |

-continued

| | | Parts by Weight | |
|---|---|---|---|
| Material # | Description | Paint A | Paint B |
| 11 | Pigment Dispersion from Example 10 | 360.2 | 265.42 |
| 12 | Deionized water | 1899.9 | 1475.48 |

[1]Available from BASF corporation
[2]Available from CECA Prochinor

For each paint, materials 1 through 8 were blended sequentially and stirred 20 minutes. Materials 9 and 10 were blended in a separate 1 gallon container for 5 minutes. The blend of materials 1-8 was then added slowly to the blend of materials 9 and 10. Materials 11 and 112 were then added sequentially.

Panel Coating

For Examples 14A and 14B, each electrodepositable coating compositions were electrodeposited onto phosphated cold rolled steel under conditions sufficient to provide an electrodeposited film thickness of about 20 micrometers. The panels were then cured for 25 minutes at different temperatures and tested for cure by acetone double rubs using ASTM D5402-6 Method A with the following exceptions: Acetone was used rather than MIBK, no water cleaning of panel, 100 double rubs are done using a cheese cloth.

Note that paint 14A required ultrafiltration to coat well. The paint was ultrafiltered 20% by weight with the filtrate being replace with deionized water. Paint 14B did not require ultrafiltration to coat well.

Example 15

Panels coated with Paint 14A and 14B were tested for acetone resistance by the double rub method described above. Panels were cured in an electric oven and in a direct fired acetone double rubs were done on each panel. If the paint failed before 100 double rubs, the number of double rubs was noted in the chart. The ratings for the rubbed area are listed below.

| Bake | Paint 14A | Paint 14B |
|---|---|---|
| 210° C./25'Gas | Pass - 100 Dar's/6 | Fail - 14 Dar's to metal |
| 160° C./25'Gas | Pass - 100 Dar's/9+ | Fail - 1 Dar's to metal |
| 150° C./25'Gas | Pass - 100 Dar's/7 | Not run |
| 210° C./25'Elec. | Pass - 100 Dar's/9 | Fail - 50 Dar's/1 |
| 160° C./25'Elec. | Pass - 100 Dar's/10 | Fail - 1 Dar's to metal |
| 150° C./25'Gas | Pass 100 Dar's/10 | Not run |

Acetone Double Rub Ratings:

1 - through to substrate in <50
2 - Through in 50-100 rubs
3 - Very severely marred. Scratches to metal easily
4 - Severely marred only over area rubbed. Can Scratch to metal
5 - Marred over rub area, can scratch through to metal
6 - Marred uniformly in center of rub area, difficult, but possible to scratch to metal
7 - Non uniform marring over rub area, can not scratch to metal
8 - Scratching, very little marring of rub area, can not scratch to metal
9 - Slight scratching of rub area, can not scratch to metal
10 - No visible damage As shown above, Paint 14A which has the cyclic guanidine catalyst resin showed good cure by solvent resistance for both gas and electric ovens. Paint 14B without any catalyst had poor cure (solvent resistance) for all cure conditions.

What is claimed is:

1. A method for preparing a cyclic guanidine comprising reacting (i) cyanamide and (ii) a polyamine, and (iii) a weak acid.

2. The method according to claim 1, wherein the (i) cyanamide comprises a dicyandiamide.

3. The method according to claim 1, wherein the (ii) polyamine comprises dipropylene triamine.

4. The method according to claim 1, wherein the method further comprises reacting (iii) a weak acid with components (i) and (ii).

5. The method according to claim 4, wherein the (iii) acid comprises a phenol, a thiol, a sulfide, a bicarbonate, a carbonate, polymerization reaction products of any of the foregoing compounds, or combinations thereof.

6. The method according to claim 5, wherein the phenol comprises bisphenol A, tert-butyl phenol, nonylphenol, polymerization reaction products of any of the foregoing compounds, or combinations thereof.

7. The method according to claim 1, wherein the reaction product of components (i) and is further reacted with an epoxy compound.

8. A method of producing a polymeric resin comprising reacting the following ingredients:
    (a) a cyclic guanidine reaction product of: (i) a cyanamide; (ii) a polyamine; and (iii) a weak acid;
    (b) an amine; and
    (c) an epoxy compound.

9. The method according to claim 8, wherein the (c) epoxy compound comprises propylene oxide, butyl glycidyl ether, phenyl glycidyl ether, glycidyl neodecanoate, or combinations thereof.

10. The method according to claim 8, wherein the (c) epoxy compound comprises a polyepoxide.

11. The method according to claim 10, wherein the polyepoxide comprises a diglycidyl ether, polymerization reaction products of diglycidyl ethers, or combinations thereof.

12. The method according to claim 11, wherein the diglycidyl ether comprises the diglycidyl ether of bisphenol A, polymerization reaction products of diglycidyl ether of bisphenol A, or combinations thereof.

13. The method according to claim 8, wherein the (ii) amine is a monofunctional amine.

14. The method according to claim 8, wherein the (ii) polyamine comprises dipropylene triamine.

15. The method according to claim 8, wherein the (iii) acid comprises a phenol, a thiol, a sulfide, a bicarbonate, a carbonate, polymerization reaction products of any of the foregoing compounds, or combinations thereof.

16. The method according to claim 8, wherein the method further comprises reacting (d) a polyamine, wherein the polyamine can be the same or different from (ii).

17. The method according to claim 8, wherein the (i) cyanamide comprises dicyandiamide.

18. A method for preparing a cyclic guanidine comprising a six-member ring, the method comprising reacting (i) cyanamide; (ii) a polyamine; and, (iii) a weak acid.

19. The method of claim 1, wherein the cyclic guanidine comprises a salt of the cyclic guanidine.

20. The method of claim 8, wherein the cyclic guanidine comprises a salt of the cyclic guanidine.

21. The method of claim 18, wherein the cyclic guanidine comprises a salt of the cyclic guanidine.

* * * * *